United States Patent [19]

Khatri

[11] Patent Number: 4,997,945

[45] Date of Patent: Mar. 5, 1991

[54] CARBAMATE SALTS OF 2-(2'-THIENYL)ALKYLAMINES

[75] Inventor: Hiralal N. Khatri, Louisville, Colo.

[73] Assignee: Syntex (U.S.A.) Inc., Palo Alto, Calif.

[21] Appl. No.: 470,018

[22] Filed: Jan. 25, 1990

[51] Int. Cl.$^5$ .................. C07D 495/04; C07D 330/20
[52] U.S. Cl. ........................................ 546/114; 549/76
[58] Field of Search ......................... 546/114; 549/76

[56] References Cited

U.S. PATENT DOCUMENTS 4,051,141 9/1977 Castaigne ........................... 546/114

*Primary Examiner*—Mary C. Lee
*Assistant Examiner*—Bernard I. Dentz
*Attorney, Agent, or Firm*—David A. Lowin; Tom M. Moran

[57] ABSTRACT

The carbamate salt of 2-(2'-thienyl)-alkylamines and particularly the ethylamine and its method of synthesis are disclosed. The carbamate salt of 2-(2'-thienyl)ethylamine is a stable, easily transportable crystalline material that can be converted to 2-(2'-thienyl)ethylamine, a useful intermediate in the synthesis of 5[(2-chlorophenyl)methyl]-4,5,6,7-tetrahydrothieno-[3,2-c]pyridine hydrochloride, also known as ticlopidine hydrochloride. The synthesis is carried out by reacting an amine of formula (I):

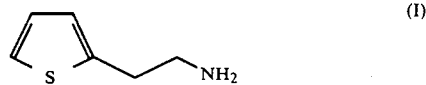

(I)

with $CO_2$ in a hydrocarbon solvent to obtain the carbamate salt of formula II:

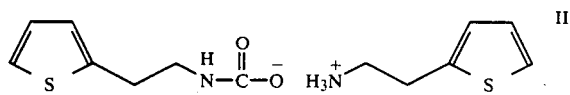

II

30 Claims, No Drawings

CARBAMATE SALTS OF 2-(2'-THIENYL)ALKYLAMINES

CROSS-REFERENCE TO RELATED APPLICATION

This application is related to a co-pending application entitled "Preparation of 2-(2'-Thienyl) ethylamine Derivatives and Synthesis of Thieno [3,2-c]pyridine Derivatives Therefrom" which application is incorporated herein by reference and which application names as inventor Brad DeHoff, a coworker in the same research organization as that of the present inventor. Said co-pending application is Ser. No. 470,299, filed contemporaneously herewith on Jan. 25, 1990.

FIELD OF THE INVENTION

This invention relates generally to the field of chemical compounds and related synthesis, purification, and isolation procedures. More particularly, this invention relates to carbamate salts of 2-(2'-thienyl)-alkylamines and to simple and efficient methods of synthesizing such carbamate salts from 2-(2'-thienyl)alkylamines, as well as methods of purifying and isolating 2-(2'-thienyl)alkylamines.

BACKGROUND OF THE INVENTION

The compound 2-(2'-thienyl)ethylamine is a known compound useful in the synthesis of a pharmaceutical drug known generically as ticlopidine hydrochloride. The compound 2-(2'-thienyl)ethylamine has the following structural formula (I):

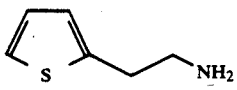

(I)

The compound of formula (I) as well as other related alkylamines of formula I(a) are not stable when subjected to an oxygen containing atmosphere.

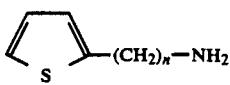

I(a)

The air instability problem with 2-(2'-thienyl)ethylamine is a serious problem in that: (1) the compound (I) is not inexpensive to produce and loss of compound (I) to oxidation increases costs; and (2) a high degree of purity is needed in the manufacture of pharmaceutical compounds. The present invention virtually eliminates the instability problem by converting the compound of formula (I) to the carbamate salt of structural formula (II).

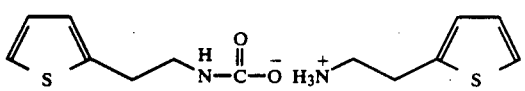

(II)

The significance of the present invention can be realized in part by referring to earlier patents disclosing ticlopidine, related compounds and their methods of synthesis.

U.S Pat. No. 4,051,141, issued Sept. 27, 1977, discloses thieno[3,2-c]pyridine derivative compounds having the formula (III):

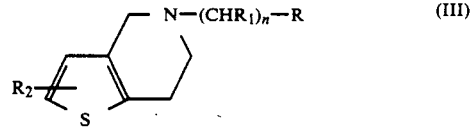

(III)

wherein R is a phenyl or benzoyl radical optionally substituted with 1-3 halogen atoms or lower alkyl, lower alkoxy, hydroxy or nitro; $R_1$ is hydrogen, halogen, hydroxy or lower alkyl; $R_2$ is hydrogen or halogen and n is 1 or 2, and in which the symbols $R_1$ may be different in each $CHR_1$ when n is 2; and their pharmaceutically acceptable acid addition salts.

Of these compounds, perhaps the most interesting is when $R_1$ and $R_2$ are H, n is 1 and R is o-chlorobenzyl. Such a compound is known chemically as 5-[(2-chlorophenyl) methyl]-4,5,6,7-tetrahydrothieno-[3,2-c]pyridine hydrochloride, more commonly known as ticlopidine and most commonly referred to as the hydrochloride salt thereof. Ticlopidine is a known and useful pharmaceutical compound.

In that the present invention includes a method for making and purifying an intermediate useful in the synthesis of ticlopidine, U.S. Pat. No. 4,051,141 is incorporated herein by reference for purposes of disclosing ticlopidine, its intermediates and related compounds as well as methods making, using and/or administering ticlopidine, its various salts, esters and related compounds. In addition, U.S. Pat. No. 4,127,580, issued Nov. 28, 1978, is incorporated herein by reference for its disclosure of ticlopidine, its intermediates and related compounds as well as methods for making such compounds. The present invention was specifically developed to aid in the synthesis of ticlopidine by improving the air stability of the intermediate of formula (I).

The compound (I) and its method of synthesis are needed to carry out the present invention. Although compound (I) is known, so that this disclosure will be self contained the following disclosure is provided regarding compound (I).

Preparation of 2-(2'-thienylethylamine (I)

2-(2'-Thienyl)ethanol (a known compound) and its suitable derivatives, e.g., benzenesulfonate and methanesulfonate are prepared according to a known procedure described by Braye in U.S. Pat. No. 4,127,580 which is incorporated herein by reference. In addition, 2-(2'-thienyl)ethanol is commercially available from Henley Chemicals, 50 Chestnut Ridge Road, Montvale, N.J., 07645.

Ammonia gas of sufficient purity, Anhydrous Grade, is commercially available from Matheson Gas Products, P.O. Box 85, East Rutherford, N.J., 07073.

Metal salts useful in the process of the present invention are represented by the formula M-Y, where M is selected from Na, Li, K, Mg, and Zn, and Y is halo or a carbonate ($CO_3{}^{-2}$) anion. These salts are commercially available, e.g., from Aldrich Chemicals, 940 West Saint Paul Avenue, Milwaukee, Wis. 53233. MgI is commercially available from Hudson Laboratories, 13923 Old Dixie Highway, Hudson, Fla. 33567.

REACTION SCHEME 1

REACTION SCHEME 1

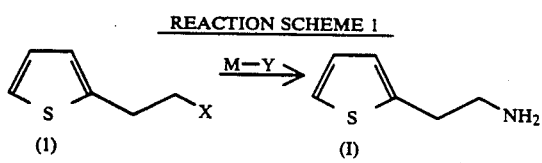

As illustrated in REACTION SCHEME 1, a suitably functionalized derivative of 2-(2'-thienyl)ethanol, i.e., a compound of Formula 1 where X is alkyl sulfonate, aryl sulfonate or halogen, preferably 2-(2'-thienyl)ethyl benzenesulfonate or 2-(2'-thienyl)ethyl methanesulfonate, and about 1 molar equivalent of a metal salt of formula M-Y is dissolved in a solvent (e.g., a polar solvent such as tetrahydrofuran, toluene, water, methanol or ethanol, preferably methanol) is placed in a pressurizable reactor. The pressure reactor is slowly pressurized to about 25–150 psi, preferably about 80 psi with ammonia gas while keeping the internal temperature at about 45°–60° C., preferably 50°–55° C., and the solution is stirred for 2–20 hours, preferably 12–16 hours, under ammonia gas.

The contents are made acidic, preferably to about pH 2, and extracted, preferably twice with a nonpolar solvent, preferably $CH_2Cl_2$. The aqueous layer is collected and made basic, preferably to about pH 10–11, and extracted, preferably three times, with a nonpolar solvent, preferably $CH_2Cl_2$. The organic layers containing the amine are combined and dried over a dessicant agent, preferably sodium sulfate, and concentrated to give the desired 2-(2'-thienyl)ethylamine as an oil.

Alternatively, water is added to the reaction mixture and the mixture is extracted three times with a nonpolar solvent (e.g., $CH_2Cl_2$) and dried over $Na_2SO_4$. The solvent is removed and the oil is purified by distillation (boiling point 90°–95° C. at 4.5 mm/Hg) or by precipitation as its carbamic acid salt as described below. Thienyl ethylamine can also be synthesized as described in U.S. application Ser. No. 192,274, filed May 10, 1988 (now U.S. Pat. No. 4,906,756) by an inventor from the same research organization as that of the present inventor, which application is incorporated herein by reference.

In pharmaceutical formulations, ticlopidine is generally in the form of ticlopidine hydrochloride having the following structural formula (IV):

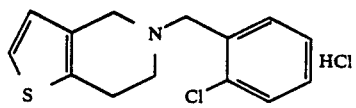

Formula IV

Pharmaceutical formulations containing ticlopidine hydrochloride have been found to possess an anti-inflammatory activity, a vasodilator activity and an inhibitor activity on blood platelet aggregation.

In that ticlopidine is a valuable pharmaceutical compound, methods of synthesizing the compound are of great commercial interest, as are methods of synthesizing, purifying and isolating intermediates useful in making ticlopidine. The present invention is directed toward such methods.

SUMMARY OF THE INVENTION

Carbamate salts and methods of synthesizing carbamate salts of 2-(2'-thienyl)alkylamines are disclosed and described herein. More specifically, the present invention discloses and describes the carbamate salt as well as a method of synthesizing the carbamate salt of 2-(2'-thienyl)ethylamine by reacting 2-(2'-thienyl)ethylamine with $CO_2$ in the presence of a hydrocarbon solvent. The invention also involves the purification and isolation of 2-(2'-thienyl)ethylamine by first producing the carbamate salt of 2-(2'-thienyl)ethylamine and reconverting the salt to 2-(2'-thienyl)ethylamine by heating to about 60° C.

A primary object of the present invention is to disclose and describe the carbamate salt of 2-(2'-thienyl)ethylamine and methods of synthesizing carbamate salts of 2-(2'-thienyl)alkylamines from 2-(2'-thienyl)alkylamines.

Another object of the present invention is to disclose and describe a method of purifying and isolating 2-(2'-thienyl)alkylamines, specifically 2-(2'-thienyl)ethylamine.

An advantage of the present invention is that the carbamate salt of 2-(2'-thienyl)ethylamine can be obtained from 2-(2'-thienyl)ethylamine by a simple efficient process.

Another advantage of the present invention is that 2-(2'-thienyl)ethylamine compounds can be quickly and economically stabilized as crystaline salts.

A feature of the present invention is that 2-(2'-thienyl)ethylamine can be converted to the carbamate salt of 2-(2'-thienyl)ethylamine by a single reaction step.

Another feature of the invention is that the carbamate salt is relatively air stable, i.e. resistant to oxidation.

These and other objects, advantages and features of the present invention will become apparent to those persons skilled in the art upon reading the details of the structure, synthesis and usage as more fully set forth herein. Reference being made to the accompanying general structural formulae forming a part hereof wherein like symbols refer to like molecular moieties throughout.

DETAILED DESCRIPTION AND PREFERRED EMBODIMENTS

Before the present process of synthesizing the carbamate salt of 2-(2'-thienyl)ethylamine, reconverting the carbamate salt of 2-(2'-thienyl)ethylamine to 2-(2'-thienyl)ethylamine and methods of using such are disclosed and described, it is to be understood that this invention is not limited to the particular amounts, temperatures, pressures, times, solvents or methods described as such may, of course, vary.

It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "an" and "the" include plural referents unless the context clearly dictates otherwise. Thus, for example, reference to "a pharmaceutically acceptable salt" includes mixtures of salts, references to "an alkylamine" includes reference to mixtures of such alkyamines, reference to "the method of synthesizing" includes one or more different methods of synthesizing which are or will become known to those skilled in the art upon reading this disclosure.

The term "pharmaceutically acceptable basic addition salts" refers to salts of the subject compounds which possess the desired pharmacological activity and which are neither biologically nor otherwise undesirable. These salts are formed with inorganic bases such as sodium hydroxide, calcium oxide; or organic bases such as triisopropyl amine, glucamine, and the like.

The term "treatment" as used herein covers any treatment of a disease and/or condition in a mammal, particularly a human, and includes:

(i) preventing the disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

"Inhibitor" as used herein refers to a compound which has the capability to restrain, stop or retard a physiologic, chemical or enzymatic action. To be an effective inhibitor, the compound must be effective in low concentration. The effectiveness of the inhibitor is determined by establishing the minimum concentration required to produce a specified degree of inhibition of the target chemical or other reaction. The lower the effective concentration, the stronger the inhibitor.

"Inhibitors of platelet aggregation" as used herein are compounds which are effective in preventing a normally caused (by bleeding or damage of endothelium of a blood vessel) or artificially caused (by an appropriate inducer) platelet aggregation. Inhibitory effect of the claimed compounds is expressed as inhibitory concentration ($IC_{50}$) and as the potency of an inhibitor.

"Inhibitory concentration ($IC_{50}$)" as used herein is the concentration of the inhibitor which is necessary to effect a 50% reduction of the aggregatory response to a standard dose of a stimulant of platelet aggregation inducer.

The invention is primarily directed to the carbamate salt of 2-(2'-thienyl)ethylamine which can be converted to 2-(2'-thienyl)ethylamine which has been found to be a useful intermediate (although unstable in air due to oxidation) in making 5-[(2'-chlorophenyl) methyl]-4,5,6,7-tetrahydrothieno-[3,2-c]-pyridine hydrochloride. The carbamate salt of 2-(2'-thienyl) ethylamine compounds is schematically described by the following general structural formula (II):

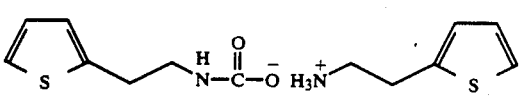

The carbamate salt of formula II can be reverted to the original amine of formula (I) by heating to about 60° C. and allowing $CO_2$ gas to evolve. The reaction of (I) to (II) and reconversion of (II) to (I), by heating, can be used to purify and isolate 2-(2'-thienyl)ethylamine of formula (I). Since the amine of formula (I) is not air stable, (i.e., it tends to oxidize in the presence of oxygen) it is convenient, useful and economical to convert (I) to (II); and thereafter reconvert (II) to (I) when (I) is to be used as an intermediate at another time in the synthesis of an end product.

The present invention is more generally applicable to the carbamate salts of the following general structural formula II(a)

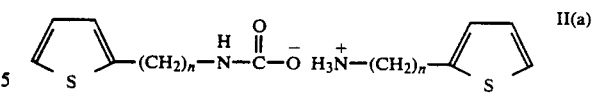

wherein n is an integer of from 2 to 5 and is most preferably 2.

The compounds of formula II(a) are obtained by reacting $CO_2$ with compounds of formula I(a).

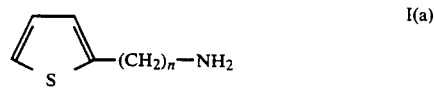

wherein n is an integer of from 2 to 5 and is most preferably 2. The reaction is carried out in a hydrocarbon solvent.

Alkylamines of formula I(a), can be used to produce carbamate salts of formula II(a) which can be reverted (by heating) to the original alkylamines of formula I(a). This production of salts of formula II(a) and reversion to the akylamines of formula I(a) can be carried out using simple, efficient processing steps.

In general the processing is carried out by first dissolving an alkylamine of formula I(a) (preferably an ethylamine of formula (I)) in a suitable hydrocarbon solvent (preferably toluene). The solution is cooled to a temperature in the range of about 10° C. to −60° C. (preferably starting at about 0° C. and decreasing the temperature as $CO_2$ is added with further cooling). The $CO_2$ is added either as solid $CO_2$ or by bubbling $CO_2$ into the solution. The $CO_2$ is added at a sufficient rate and for a sufficient period of time to allow for the $CO_2$ to contact with the amine molecules in the solution so that the carbamate salt is formed. The carbamate salt of formula II(a) will form and precipitate out of solution as crystals. The crystals can be separated by filtration and then washed with the hydrocarbon solvent and dried under vacuum. The dried salt crystals of the carbamate salt can be reverted to the alkylamine by heating. Crystals of the carbamate salt of formula II are reverted to formula I by heating the salt crystals to about 60° C.

Preparation of 5[(2-chlorophenyl) methyl]-4,5,6,7-Tetrahydrothieno[3,2c]pyridine (Ticlopidine hydrochloride is shown as formula (IV) above.)

4,5,6,7-Tetrahydrothieno[3,2-c]pyridine (prepared in steps 1 and 2 below) can be prepared according to the procedure of Gronowitz et al. [Arkiv Kemi, 11(19), 217-227 (1970)] incorporated herein by reference. An example of a useful synthesis of ticlopicline hydrochloride is given below.

REACTION SCHEME 2

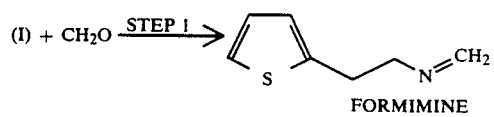

FORMIMINE

-continued
REACTION SCHEME 2

FORMIMINE + dil. acid $\xrightarrow{\text{STEP 2}}$ 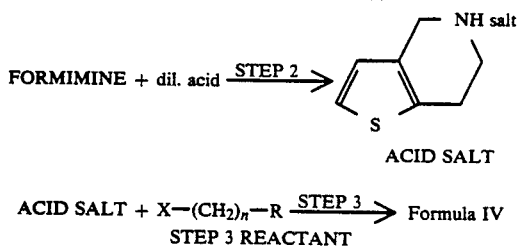

ACID SALT

ACID SALT + X—(CH$_2$)$_n$—R $\xrightarrow{\text{STEP 3}}$ Formula IV
STEP 3 REACTANT Wherein R of the STEP 3 REACTANT is defined above in connection with formula III and is a phenyl or benzoyl radical optionally substituted with 1-3 halogen atoms or lower alkyl, lower alkoxy, hydroxy or nitro and in order to obtain the desired end product of formula IV R is o-chlorobenzyl. The compound of formula IV is ticlopidene hydrochloride the structure of which was shown above. The n of the STEP 3 REACTANT is 1.

The overall reaction scheme for making ticlopidine is shown above in order to explain how the present invention can be utilized in connection with a reaction scheme for the synthesis of ticlopidine. In connection with REACTION SCHEME 2 above it should be noted that the essence of the present invention has been completed (as described earlier) by converting the compound (I) to the salt (II). The salt (II) could be used in place of the compound (I) in REACTION SCHEME 2 as the salt II will revert it to the compound (I) by heating the salt (II) in the formaldehyde in STEP 1. Alternatively, the salt (II) can be reconverted to (I) and then used as a starting material as shown in the above REACTION SCHEME 2. The individual STEPS 1-3 shown above are known (although without the use of the salt (II). However, so that this disclosure will be self-contained, the STEPS 1-3 are described below and a specific indication is given as to how the salt (II) is utilized.

STEP 1

A slight molar excess of formaldehyde (e.g., a 37% aqueous solution) is added dropwise with stirring to a slurry of 2-(2'-thienyl)ethylamine carbamate salt of formula II in water (which forms the amine of formula I. The reaction mixture is stirred for about 1 to 5 hours, preferably about 3 hours, at 60°-65° C. After cooling to room temperature, the product is extracted, e.g., into toluene (or another solvent such as dichloromethane, chloroform, or ethyl acetate), washed and concentrated in vacuo to give the formimine of 2-(2'-thienyl)ethylamine. The formine of other alkylamines can be obtained in a similar fashion by using another carbamate salt of formula II(a) which will revert to another alkylamine of formula I(a).

STEP 2

The formimine compound obtained as described above is shaken with a dilute solution of an aqueous acid (such as hydrochloric acid or sulfuric acid) or a solution of the formimine dissolved in an organic solvent such as THF or toluene, preferably THF, is shaken with an organic acid (such as formic acid, oxalic acid, paratoluene sulfonic acid or methane sulfonic acid; preferably methane sulfonic acid) for 3 to 10 hours, preferably about 6 hours. The mixture is then basified (e.g., with NaOH) and extracted, e.g., with methylene chloride (or another solvent). The extracts are washed and concentrated in vacuo to give 4,5,6,7-tetrahydrothieno[3,2-c]pyridine referred to as the ACID SALT in REACTION SCHEME 2.

STEP 3

Preparation of Ticlopidine Formula IV

Still referring to REACTION SCHEME 2, a solution of 4,5,6,7-tetrahydrothieno[3,2-c]pyridine (i.e., the ACID SALT) in a solvent (e.g., a polar solvent, such as THF, dichloromethane or acetonitrile; preferably THF) is added to a molar excess of a suspension of a base (e.g., a metal hydride, such as lithium hydride, 50% sodium hydride, or potassium hydride; preferably, 50% sodium hydride) in the same or a similar solvent. The mixture is stirred at a temperature of about 15° to 30° C., preferably about room temperature for about 10 minutes to about 2 hours, preferably about 30 minutes and a slight molar excess (e.g., a ratio of about 1.1 to 0.7) of an optionally substituted phenalkyl or phenacyl halide (STEP 3 REACTANT) [where X is halo, n is 1 or 2, and R is a phenyl or benzoyl radical optionally substituted with 1-3 halogen atoms or alkyl having 1-6 carbon atoms, alkoxy having 1-6 hydroxy or carbon atoms, or nitro, (for example the halides of Formula III in U.S. Pat. No. 4,051,141, such as 4-methoxybenzyl chloride, phenacyl bromide, or preferably o-chlorobenzyl chloride)]is added.

After stirring at about room temperature, for about 1 to 2 hours, preferably about 90 minutes, the mixture is heated, preferably to the reflux temperature of the solvent used. Another solvent (e.g., toluene, xylene, or ether; preferably toluene) is added and the mixture is further refluxed for about 2 to 48 hours, preferably for about 10 to 30 hours, most preferably about 20 hours. The mixture is then cooled to about room temperature and acidified (e.g, with dilute hydrochloric acid or acetic acid; preferably hydrochloric acid).

The organic layer is separated, the aqueous layer is extracted (e.g., with toluene, dichloromethane, ethyl acetate, or i-propyl acetate; preferably toluene) and the combined aqueous layers are basified (e.g., with aqueous NaOH or solid NaOH) to a pH of about 13-14. The product is extracted, e.g., into methylene chloride (or another solvent). The extracts are washed (e.g., with water optionally including a salt solution), dried and then concentrated in vacuo to give a compound of Formula IV.

When the compound of the STEP 3 REACTANT is o-chlorobenzyl chloride, ticlopidine free base (Formula IV) is formed (about 80% yield) as a light yellow oil.

Phase Transfer Alkylation

Alternatively, the alkylation can be performed under phase transfer conditions, e.g., as described in GB 2,166,730, the pertinent parts of which are incorporated herein by reference to disclose such phase transfer alkylation. The 4,5,6,7-tetrahydrothieno[3,2-c]-pyridine (ACID SALT) and the compound shown as the STEP 3 REACTANT (preferably o-chlorobenzyl chloride) are dissolved in a solvent system (preferably an aqueous:organic two-phase solvent system, the organic phase of which is immiscible with water, e.g., hydrocarbons such as benzene, toluene and xylene; and ethers such as isopropyl ether and diethyl ether; preferably toluene) combined with a phase transfer catalyst [e.g., a quaternary ammonium salt, such as trimethylbenzyl ammonium hydroxide, hydrogen sulfate tetra-n-butyl ammonium, trioctylmethyl ammonium chloride, triethylbenzyl ammonium chloride or tert-butyl ammonium iodide ("TBAI"), or a phosphonium salt, such as tetrabutyl phosphonium chloride, or a crown ether, such as 18-crown-6 or dibenzo 18-crown-6; preferably TBAI] in the presence of a base [e.g., sodium hydroxide, potassium hydroxide, lithium hydroxide, potassium carbonate, sodium carbonate, or sodium hydride; preferably sodium hydroxide] and stirred for about 24 to 72 hours, preferably about 40 hours, at room temperature. The product (75% of theoretical yield) is separated, concentrated, and purified by the usual means.

Preferred Alkylation

In a preferred alkylation procedure, 4,5,6,7-tetrahydrothieno[3,2-c]pyridine in a solvent (e.g., a polar solvent, such as THF, dichloromethane or acetonitrile; preferably 5-15% wet THF) and a compound referred to as the STEP 3 REACTANT (preferably o-chlorobenzyl chloride) are added to a molar excess of a base (e.g., potassium carbonate, sodium carbonate, or lithium carbonate; preferably potassium carbonate) that has been wetted with water (about 5 to 15%, preferably about 10% of the volume charge) and the reaction mixture is refluxed until disappearance of the starting materials is confirmed by tlc (about 8 to 42 hours, preferably about 18-24 hours). The solvent is removed (by vacuum or by displacement with another solvent such as toluene), and the product is washed with water and then concentrated in vacuo. Using the preferred compound, i.e. o-chlorobenzyl chloride STEP 3 REACTANT, ticlopidine free base (shown in Formula IV as the hydrochloride) is formed (about 90-95% yield) as a light yellow oil.

Alternate Preparation of Formula IV
REACTION SCHEME 3

REACTION SCHEME 3

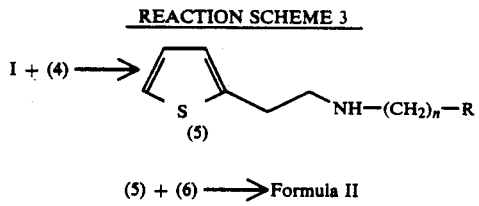

$I + (4) \longrightarrow$ (5)

$(5) + (6) \longrightarrow$ Formula II

[The compound of formula (4) is the STEP 3 REACTANT described above in connection with REACTION SCHEME (II). The compound (6) is used to cyclized the tail of the compound (5) and may be formaldehyde, paraformaldehyde, trioxane and other chemically similar compounds such as dimethorymethane.]

Alkylation of 2-(2'-thienyl)ethylamine, Followed by Cyclization

Another alternative preparation of the free base of compounds of Formula IV is illustrated above in REACTION SCHEME 3, where the compound of Formula I, prepared as described above with reference to REACTION SCHEME 2, is contacted with the STEP 3 REACTANT preferably o-chlorobenzyl chloride (under the conditions described above) to give the secondary amine of Formula (5). The compound of formula (5) is in turn cyclized by contacting it with a compound identified in the above REACTION SCHEME 3 as Formula (6) (i.e., formaldehyde, paraformaldehyde, trioxane or a compound identified in U.S. Pat. No. 4,174,448 as Formula III, such as dimethoxymethane) under the conditions described in U.S. Pat. No. 4,174,448, the pertinent portions of which are incorporated herein by reference.

Preparation of the Salts of Formula IV

The free base compound of Formula IV may be converted to acid addition salts such as the hydrochloride salt shown in Formula IV. The conversion is accomplished by treating the free base with a stoichiometric amount of an appropriate acid, such as hydrochloric acid, sulfuric acid, methanesulfonic acid, HBr, or the like (for tyclopidine the preferred acid is hydrochloric). Typically, the free base is dissolved in a polar organic solvent such as ethanol or methanol, and the acid is added in water, ethanol or methanol. The temperature is maintained at 0°-50° C. The resulting salt precipitates spontaneously or may be brought out of solution with a less polar solvent (such as toluene, ether, or ethyl acetate; preferably toluene).

Preferably, for making ticlopidine hydrochloride, about 1.3 equivalents of gaseous hydrogen chloride is bubbled into isopropanol, which is then added slowly with stirring to ticlopidine free base in toluene, maintaining the temperature below about 40° C. during the addition. The stirring is continued for about 30 to 90 minutes, preferably about 1 hour at about 45°-50° C., followed by cooling to about 5°-10° C. for about 30 to 90 minutes, preferably about 1 hour, and the ticlopidine hydrochloride precipitates. It is isolated (e.g., by centrifugation), digested (e.g., with toluene and isopropanol, or preferably with acetone), dried (e.g., at about 65° to 70° C. under vacuum), and recrystallized from a lower alkanol (e.g., methanol, ethanol or isopropanol).

The acid addition salt compounds such as the hydrochloride salt of Formula IV may be converted to the corresponding free bases by treating with an excess of a suitable base, such as ammonia or sodium bicarbonate, typically in the presence of aqueous solvent, and at a temperature of between 0° and 50° C. The free base form is isolated by conventional means, such as extraction with an organic solvent.

PREFERRED PROCESSES AND LAST STEPS
THE ETHYLAMINE (I)

A preferred process for making 2-(2'-thienyl)ethylamine, comprises reacting a suitably functionalized derivative of 2-(2'-thienyl)ethanol, more preferably the benzenesulfonate or methanesulfonate, with ammonia gas in the presence of a metal salt, preferably NaBr. This preferred process is described in detail in the copending application referred to above in the CROSS-REFERENCE section.

THE CARBAMATE SALT II

The ethylamine of formula (I) is included in a toluene solvent. The solution is cooled to 0° C. Cooling of the solution is continued as $CO_2$ is bubbled into the solution until the precipitation of the carbamate salt crystal ceases. The crystals are removed (e.g., by filtration), washed (e.g., with toluene) and dried (e.g., by vacuum evaporation).

TICLOPIDINE

A preferred process for making ticlopidine comprises the steps of:

a. reacting a suitably functionalized derivative of 2-(2'-thienyl)ethanol with ammonia gas in the presence of a metal salt to give 2-(2'-thienyl)ethylamine (as indicated above), and b. converting the 2-(2'-thienyl)ethylamine to ticlopidine (having stored the ethylamine as its carbamate salt before use in order to reduce its oxidation).

In the above-described generalized process for making ticlopidine, further preferred is the process wherein the step of converting the 2-(2'-thienyl)ethylamine to ticlopidine comprises the steps of:

c. heating and contacting the carbamate salt of 2-(2'-thienyl)ethylamine with formaldehyde to give the formimine;

d. cyclizing said formimine by contacting it with an aqueous mineral acid to form 4,5,6,7-tetrahydrothieno[3,2-c]pyridine; and e. alkylating said 4,5,6,7-tetrahydrothieno-[3,2-c]pyridine to give ticlopidine, by contacting it with o-chlorobenzyl chloride under either:
  (i) phase transfer conditions, or
  (ii) preferably, by reflux with a base, most preferably potassium carbonate, using conventional alkylation conditions.

In the above processes the present invention is utilized when the 2-(2'-thienyl)ethylamine is converted to its carbamic acid salt for storage, transportation, handling and/or further purification, and may be used directly (as described above) or converted back to 2-(2'-thienyl)ethylamine for subsequent use in step c above. In the above described step c the stable carbamate salt is added directly to the reaction solution where it will convert to the 2-(2'-thienyl)ethylamine, i.e. the carbamate salt is not heated separately and converted to the ethylamine before adding it to the reaction.

In connection with the above processes it is preferable to use the additional step of converting the ticlopidine free base so-made to the hydrochloride salt.

Preferred Compound

The carbamate salt of 2-(2'-thienyl)-ethylamine is the most preferred compound of the invention and is preferably used in a process to make 5-(2-chlorobenzyl)-4,5,6,7-tetrahydrothieno[3,2-c]pyridine, which is also known as ticlopidine and the hydrochloride salt thereof.

EXAMPLES

The following examples are provided so as to provide those of ordinary skill in the art with a complete disclosure and description of how to make the carbamate salt compounds of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, temperature is in degrees C, and pressure is at or near atmospheric.

EXAMPLE 1

Add carbon dioxide to a solution of a 2-(2'-thienyl)alkylamine in a hydrocarbon solvent maintained at a temperature in the range of 10° C. or less, but above the freezing temperature of the solution. Allow crystals of carbamate salt to form by reducing the temperature as needed and stirring. Crystals of the carbamate salt will precipitate out of the solution. Isolate the crystals by any suitable means such as filtration. Dry the isolated crystals by any means known to those skilled in the art such as applying a vacuum. Store the dried crystals for future use. The crystals are substantially more stable than the 2-(2'-thienyl) ethylamine - more specifically the crystals are resistant to oxidation on exposure to air.

EXAMPLE 2

Add solid carbon dioxide (dry ice) to a solution of 2-(2'-thienyl)ethylamine (20.0 g) in toluene (150 ml) with an initial temperature of 0° C. decreasing as the dry ice is added. The $CO_2$ will bubble to the surface and react with the ethylamine forming the carbamate salt of formula II which salt will precipitate out of the solution as crystals after stirring the solution for about 30 minutes. Filter the crystals away and dry under a vacuum at 30° C. The yield will approach 100%.

EXAMPLE 3

Bubble gaseous $CO_2$ at 0° C. into a solution of 2-(2'-thienyl)ethylamine in a combination solution of toluene/hexane 1:1. Continue the bubbling while stirring and maintaining the temperature at 10° C. or less until crystals stop forming and precipitating out of solution. Isolate the precipitated crystals by filtration and dry the isolated crystals under vacuum.

ANALYSIS

The structural formula II and II(a) shown above for the carbamate salt are proposed structures based on the best available information. However, the carbamate salt of the present invention is a new compound and its precise structure is not known for a certainty. The salt crystals are in a powder form which would make X-ray diffraction analysis difficult. Since NMR and IR do not conclusively establish structure, an elemental analysis was completed to obtain the following results:

|   | % Calculated | % Found |
|---|---|---|
| C | 52.35 | 52.39 |
| H | 6.09 | 6.04 |
| N | 9.11 | 9.40 |
| S | 21.40 | 21.47 |

Salt samples analyzed gave 98-100% of the theoretical amine value. These results strongly indicate that the structure shown as II and II(a) are correct.

The carbamate salt of 2-(2'-thienyl)ethylamine of this invention was tested by heating and found to be reconverted to 2-(2'-thienyl)ethylamine and this amine was found to be useful in synthesizing ticlopidine and ticlopidine hydrochloride, i.e., 5[(2-chlorophenyl)-methyl]-4,5,6,7-tetrahydrothieno [pyridine hydrochloride].

Example A

Preparation of Ticlopidine

A-1. Formimine of 2-(2'-Thienyl)ethylamine

A 37% aqueous formaldehyde solution (2.7 g, 0.033 mole) is added dropwise with stirring to 3.4 g (0.027 mole) of 2-(2'-thienyl)ethylamine obtained, e.g., by warming 4 g (0.0135 mole) of carbamic acid salt (2 mole of amine/mole of salt) in 8 ml of $H_2O$ at 45° C. The reaction mixture is stirred for three hours at reflux. After cooling to room temperature, the product is extracted into toluene (2×50 ml); the toluene extracts are washed with water (50 ml) and concentrated to give the desired product.

Following the above procedure, there is obtained 3.4 g (91%) of the formimine of 2-(2'-thienyl)ethylamine. Reported NMR (CDCl$_3$) w: 7.2–6.8 (m,3H), 3.46 (s,2H), 3.0–2.7 (m,4H).

A-2. 4.5,6,7-tetrahydrothieno 3,2-c pyridine

The formimine of 2-(2'-thienyl)ethylamine, prepared, for example, as described in Example A-1 is shaken with 7 ml of 6N hydrochloric acid for six hours. The mixture is basified with 60 ml sodium hydroxide and extracted with 3×70 ml methylene chloride. The methylene chloride extracts are washed with water (1×50 ml) and concentrated to give the desired product.

Following the above procedure, there is obtained 3.4 g (about 100%) of crude, 4,5,6,7-tetrahydrothieno-[3,2-c]pyridine. Reported NMR (CDC13) w: 7.06 (d,1H), 6.72 (d,1H), 3.9 (br.s,2H), 3.2–2.7 (m,4H), 2.10 (br.s,-NH).

A-3. Ticlopidine Free Base

To a suspension of sodium hydride (0.42 g, 8.6 mmole) in THF (5.0 ml) is added a solution of 4,5,6,7-tetrahydro-thieno[3,2-c]pyridine (1.0 g, 7.2 mmole), prepared, for example, as described in Example A-2, in THF (10 ml). The mixture is stirred under a nitrogen atmosphere at room temperature for 30 minutes and o-chlorobenzyl chloride (1.74 g, 10.8 mmole) is added. After stirring at room temperature for 90 minutes, toluene (15 ml) is added and the mixture is heated to reflux for 15 to 20 hours. Disappearance of starting material is confirmed by TLC. The mixture is then cooled to room temperature and acidified with 40 ml 1N hydrochloric acid. The organic layer is separated. The aqueous layer is extracted with 50 ml of toluene. The aqueous layer is then separated and basified with dilute aqueous sodium hydroxide to pH 13-14. The product is extracted into methylene chloride (3×40 ml). The methylene chloride extracts are washed (1×50 ml water) and 1×50 ml salt solution) then dried over anhydrous magnesium sulfate and concentrated to give the desired product.

Following the above procedure, there is obtained 1.5 g (80%) of 5-(2-chlorobenzyl)-4,5,6,7-tetrahydrothieno[3,2-c]pyridine (ticlopidine free base) as a light yellow oil.

Reported NMR (CDCl$_3$) w: 7.7–7.15 (m,4H), 7.05 (d,1H), 6.65 (d,1H), 3.8 (s,2H), 3.6 (s,2H), 2.85 (br.s,4H).

A-4. Ticlopidine Hydrochloride

Gaseous HCl (0.22 g, 0.006 mole) is bubbled into 50 ml isopropanol. The resulting solution is added dropwise to ticlopidine free base (1.5 g, 0.005 mole) in 50 ml toluene, prepared, for example as described in Example A-3, maintaining the temperature below 40° C. during the addition. The reaction mixture is stirred for 1 hour, colled to about 5°–10° C. for 1 hour, and the precipitate separated by centrifugation. An acetone slurry is made of the precipitate, brought to reflux for 1 hour, and cooled to about 5°–10° C. for 1 hour. The precipitate, ticlopidine hydrochloride (Formula IV), is separated by centrifugation, dried at 65°–70° C. under vacuum, and recrystallized from methanol. (m.p. 206.5°–207.5° C.)

A-5. Other Compounds of Formula III

By following the procedure of Example A-3 and substituting for 0-chlorobenzyl chloride the following:
m-chlorobenzyl chloride,
0-bromobenzyl bromide,
3,4,5-trimethoxybenzyl chloride,
phenacyl bromide, and
o-methoxyphenacyl bromide;
there are obtained the following respective compounds:
5-(3-chlorobenzyl)-4,5,6,7-tetrahydrothieno[3,2-c]pyridine,
5-(2-bromobenzyl)-4,5,6,7-tetrahydrothieno[3,2c]pyridine,
5-(3,4,5-trimethoxybenzyl)-4,5,6,7-tetrahydrothieno[3,2-c]pyridine,
5-phenacyl-4,5,6,7-tetrahydrothieno[3,2-c]pyridine, and
5-(o-methoxyphenacyl)-4,5,6,7-tetrahydrothieno[3,2-c]pyridine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for making a carbamate salt of 2-(2'-thienyl)alkylamine, comprising the steps of:
reacting a solution of 2-(2 -thienyl) alkylamine dissolved in a solvent with $CO_2$;
allowing the reaction between 2-(2'-thienyl) alkylamine and $CO_2$ to proceed and provide a reaction product of the carbamate salt of 2-(2'-thienyl)alkylamine; and
isolating and obtaining the carbamate salt of 2-(2'-thienyl)alkylamine.

2. The method as claimed in claim 1, wherein the 2-(2'-thienyl)alkylamine is 2-(2'-thienyl)ethylamine.

3. The method as claimed in claim 1, wherein the $CO_2$ is added to the solution in a solid form.

4. The method as claimed in claim 1, wherein the 2-(2'-thienyl)ethylamine is in a hydrocarbon solvent.

5. The method as claimed in claim 4, wherein the hydrocarbon solvent is selected from the group consisting of toluene, hexane, cyclohexane, octane and mixtures thereof.

6. The method as claimed in claim 1, wherein the $CO_2$ is added to the solution in the form cf a gas which is bubbled through the solution.

7. The method as claimed in claim 1, wherein the reacting is carried out at a temperature in the range of 10° C. to a temperature above the freezing point of the solution.

8. The method as claimed in claim 7, wherein the temperature is in the range of 0° C. to −60° C.

9. The method as claimed in 1, wherein the 2-(2'-thienyl)alkylamine is 2-(2'-thienyl) ethylamine, the solvent is a hydrocarbon solvent selected from the group consisting of toluene, hexane, cyclohexane, octane and mixtures thereof and the reacting is carried out at a temperature in the range of 0° C. to −60° C.

10. A carbamate salt having the structural formula II(a):

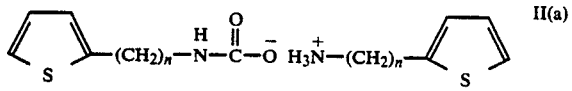

(II(a))

wherein n is an integer of from 2 to 5.

11. The carbamate salt as claimed in 10, wherein n is 2.

12. A method of purifying a 2-(2'-thienyl)alkylamine dissolved in a solvent and forming a solution with other solutes, comprising the steps of:
contacting the solution with carbon dioxide in order to form a carbamate salt of a 2-(2'-thienyl)alkylamine;
continuing the contacting until the formed carbamate salt has precipitated out of the solution; and
isolating the precipitated salt from the solution.

13. The method as claimed in claim 12, wherein the 2-(2'-thienyl)alkylamine is 2-(2'-thienyl) ethylamine.

14. The method as claimed in claim 12, wherein the carbon dioxide is contacted with the solution by adding solid carbon dioxide to the solution.

15. The method as claimed in claim 12, wherein the carbon dioxide is contacted with the solution by bubbling gaseous carbon dioxide into the solution.

16. The method as claimed in claim 12 wherein the solvent is a hydrocarbon solvent.

17. The method as claimed in claim 16 wherein the solvent is a hydrocarbon solvent selected from the group consisting of toluene, hexane, cyclohexane, octane and mixtures thereof and wherein the contacting of the solution and the carbon dioxide is carried out at a temperature in the range of 0° C. to −60° C.

18. A process for making ticlopidine, comprising the steps of:
contacting 2-(2'-thienyl)ethylamine prepared from the carbamate salt of 2-(2'-thienyl) ethylamine with formaldehyde to give the formimine;
cyclizing said formimine by contacting it with aqueous hydrochloric acid to form 4,5,6,7-tetrahydrothieno[3,2-c]pyridine; and
alkylating said 4,5,6,7-tetrahydrothieno[3,2-c]pyridine to give ticlopidine, by contacting it with o-chlorobenzyl chloride under either:
(i) phase transfer conditions, or
(ii) by reflux with a base.

19. The process for making ticlopidine of claim 18 wherein said alkylation comprises contacting said 4,5,6,7-tetrahydrothieno[3,2-c]pyridine with a base selected from the group including potassium carbonate, sodium carbonate and lithium carbonate, using conventional alkylation conditions.

20. The process of claim 18 further comprising: converting said ticlopidine to a hydrochloride salt.

21. The process of claim 19 further comprising: converting said ticlopidine to the hydrochloride salt.

22. A process for making ticlopidine, comprising the steps of:
(a) contacting a solution of a solvent having dissolved therein 2-(2'-thienyl)ethylamine with carbon dioxide in order to form a carbamate salt of 2-(2'-thienyl)ethylamine;
(b) continuing the contacting until the formed carbamate salt has precipitated out of the solution;
(c) isolating the precipitated carbamate salt from the solution;
(d) contacting the carbamate salt with formaldehyde to give the formimine of 2-(2'-thienyl)ethylamine;
(e) cyclizing said formimine by contacting it with aqueous hydrochloric acid to form 4,5,6,7-tetrahydrothieno[3,2-c]pyridine; and
(f) alkylating said 4,5,6,7-tetrahydrothieno-[3,2-c]pyridine to give ticlopidine, by contacting it with o-chlorobenzyl chloride under either:
(i) phase transfer conditions, or
(ii) by reflux with a base.

23. The method as claimed in claim 22, wherein the carbon dioxide is contacted with the solution by adding solid carbon dioxide to the solution.

24. The method as claimed in claim 22, wherein the carbon dioxide is contacted with the solution by bubbling gaseous carbon dioxide into the solution.

25. The method as claimed in claim 25 wherein the solvent is a hydrocarbon solvent.

26. The method as claimed in claim 25 wherein the solvent is a hydrocarbon solvent selected from the group consisting of toluene, hexane, cyclohexane, octane and mixtures thereof and wherein the contacting of the solution and the carbon dioxide is carried out at a temperature in the range of 0° C. to −60° C.

27. The method as claimed in claim 22 wherein the carbamate salt of step (c) is converted to 2-(2'-thienyl)ethylamine which is then used in step (d) to react with formaldehyde to give the forminine.

28. The reaction product of 2-(2'-thienyl) ethylamine and carbon dioxide contacted in a hydrocarbon solvent.

29. The reaction product as claimed in claim 28, wherein the carbon dioxide is gaseous.

30. The reaction product as claimed in claim 28, wherein solid carbon dioxide is added to said solvent with the 2-(2'-thienyl)ethylamine dissolved therein.

* * * * *